United States Patent [19]

Kole, Jr.

[11] Patent Number: 4,728,293

[45] Date of Patent: Mar. 1, 1988

[54] LEARNING DEVICE

[76] Inventor: James S. Kole, Jr., 421 San Bruno, Garland, Tex. 75043

[21] Appl. No.: 42,832

[22] Filed: Apr. 27, 1987

[51] Int. Cl.$^4$ ............................................. G09B 19/00
[52] U.S. Cl. .................................................. 434/236
[58] Field of Search ......................................... 434/236

[56] References Cited

U.S. PATENT DOCUMENTS 3,158,431 11/1964 Gutjahr et al. ...................... 434/236
4,671,772 6/1987 Slade .................................... 434/236

Primary Examiner—Gregory E. McNeill
Attorney, Agent, or Firm—James C. Fails; Wm. T. Wofford; Arthur F. Zobal

[57] ABSTRACT

A learning device, including an induced gravitational force accelerator and decelerator exerciser with adjustable seats for stressing the cells of the body characterized by support for supporting the body and a reciprocally movable apparatus connected with the support for moving the support and the body reciprocally vertically to effect an accelerational and gravitational force stress on the cell above the effect of 1 G, and educational message apparatus for introducing a learning message, either audibly or visibly, or both to the person whose body is being stressed, the video being susceptible to being turned on to flash the message when the gravitational force exceeds 1.0 G on the body cells such that learning occurs at an increased rate and with increased retention.

5 Claims, 10 Drawing Figures

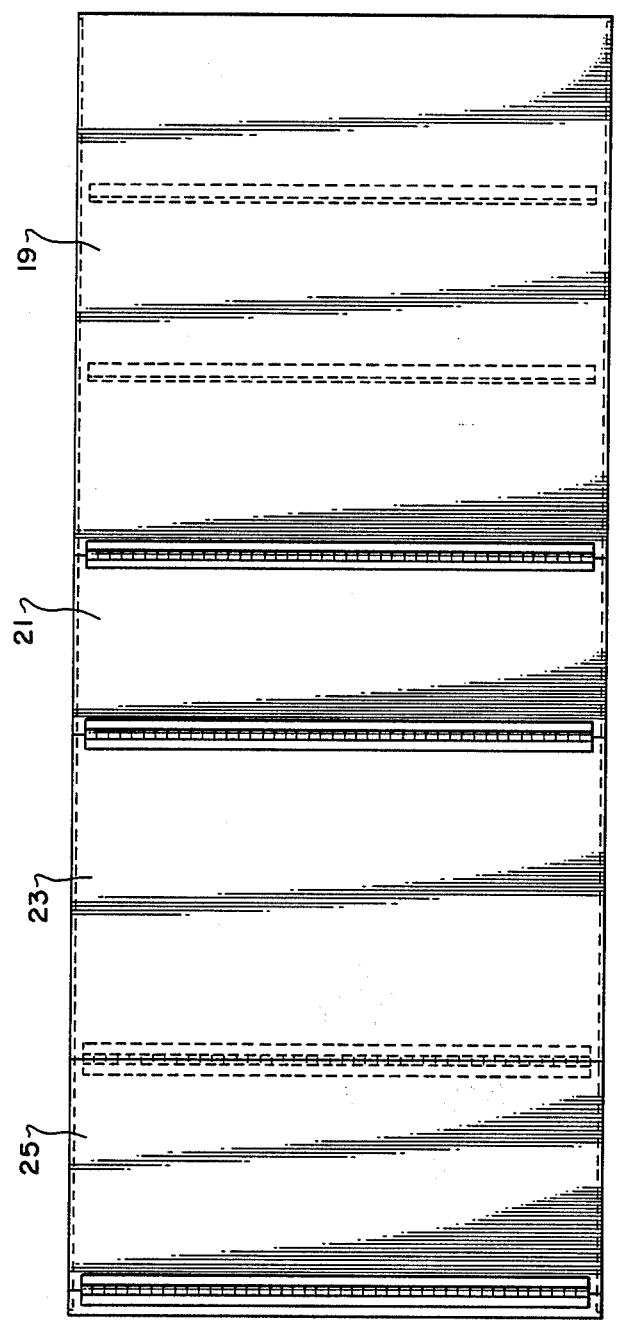
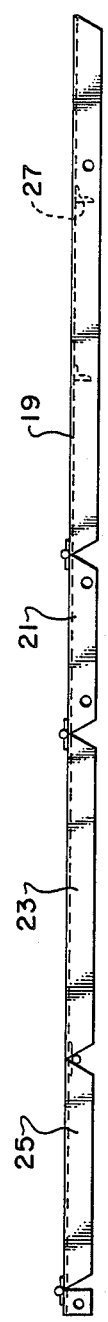
Fig. 5
Fig. 6

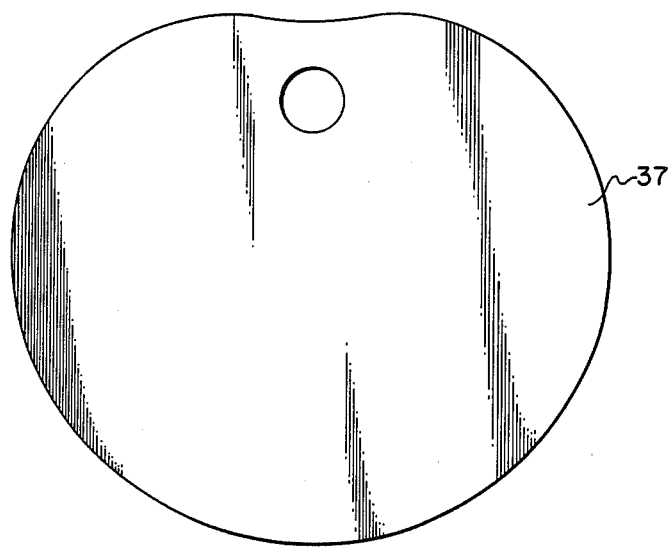
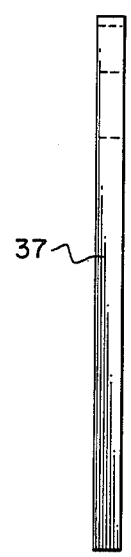
Fig. 7A                Fig. 7B
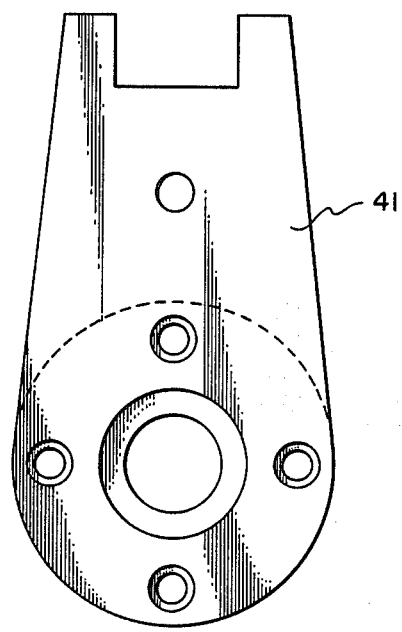
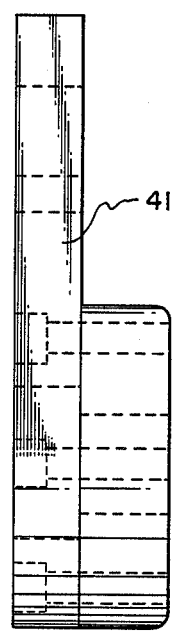
Fig. 8A                Fig. 8B

LEARNING DEVICE

FIELD OF THE INVENTION

This invention relates to a learning device; and more particularly, to a device that incorporates an induced gravitational force accelerator/decelerator type exerciser for stressing the cells of the body with an acceleration and gravitational force greater than normal and means for imparting to the person a message to be learned in discernible form during the time of the stressing of the cells above normal.

BACKGROUND OF THE INVENTION

Recognition that cells respond to their accelerational and gravitational force stimuli is relatively new. Consequently, the background for this invention, if properly interpreted is relatively new. It has been recognized for some years that jogging effects desirable aerobic benefits, as well as increased stress resistance by the cells of the body of the jogger. On the other hand, recent NASA (National Aeronautics and Space Agency) experiments in weightless outer space have indicated a weakening of the cells from the reduced gravitational effects. A relatively new book entitled "THE MIRACLES OF REBOUND EXERCISE," Albert E. Carter, The National Institute of Reboundology and Health, Inc., 1979, Edmonds, Wash., 98020, shows beneficial effects of stressing cells by increased gravitational force during rebound, such as jumping on a trampoline. The problems of this prior art has been that the jogger, or rebounder may suffer from lower back problems or other physical debilities that are worsened by the types of exercises being employed. They have provided no substitute.

Books are available to indicate that the mind can be reprogrammed and that there can be a conscious refocusing to improve learning. Typical of such books is "GATHERING POWER Through Insight and Love," Ken Keys, Jr., Penny Keys and staff, First Edition, Living Love Publications, Koos Bay, Oreg. 97420, 1987, which shows methods that can be used daily to improve self and relationships with others.

There have been a plurality of studies made on reprogramming the subconsious. Illustrative of these type approaches is the booklet and program entitled "SUBLIMINAL SUGGESTION AND SELF-HYPNOSIS PROGRAMS FOR YOUR COMPUTER.", Michael Anderson, 1984, Greentree Publishers, 5364 Ashwood, Camarillo, Calif. 93010. The software for this program was developed by Lonny McKinnon. It is touted as a modern tool for self improvement and includes software for IBM PC computers and other compatible computers. Therein is disclosed the programming of a computer to flash a message on a video display terminal so rapidly that it is not perceptible to the conscious mind. That written material refers to others in this area, including "THE HIDDEN MESSAGE THAT BREAKS HABITS," R. C. Morse and David Stoller, Science Digest, September, 1982 and "THE HIDDEN PERSUADERS," by Vance Packard.

An article appeared in the "WALL STREET JOURNAL" of Dec. 5, 1984 entitled "THE LAST FRONTIER OF THE PROGRAMMERS IS ALL IN YOUR MIND." That article describes the program on subliminal suggestion and how it can be used in different ways by causing a computer screen to flash the message subliminally to the viewer.

If merely the structural aspect of the apparatus for effecting the reciprocal movement is considered, there are several prior art references that are pertinent. For example, U.S. Pat. No. 3,480, "Exercising Machine," Halstead, was patented in 1844, more than one hundred and forty years ago and describes an exercising machine that can be cranked by hand or the like to rotate a wheel that has protrusions which strike a bar to move a seat in order to simulate the rocking motion of riding horseback so that the patient may relax the abdominal muscles. U.S. Pat. No. 14,186 shows a double acting pump that employs cam shafts to impart vibratory motion to lift buckets for pumping. U.S. Pat. No. 17,721 is a more than one hundred and twenty year old patent and describes an ore jigger having a hand crank for separating metal with sieves and the like. U.S. Pat. No. 45,230 shows a method of converting motion and is more than one hundred and twenty years old. U.S. Pat. No. 316,938 shows a paper pulp screen that can be vibrated. U.S. Pat. No. 897,791, describes a vibrating bed in which a vibrator is in contact with a bed to effect vibrations of a very minor amplitude. U.S. Pat. No. 941,671 describes an electrovibratory couch employing a rapidly vibrating means driven by a motor such that motion is a to-and-fro motion that avoids imposing any vertical motion. U.S. Pat. No. 941,673 describes an electrovibratory couch to provide a smooth undulatory motion in distinction to a severe motion such as would be produced by a cam or the like; and has no teaching of producing 2G's for sufficiently stressing the cells to attain enhanced performance of the cells. U.S. Pat. No. 1,017,840 describes a therapeutic vibrator having a speed of 3,000 revolutions per minute or more and employing an unbalanced weight to impart the vibrations to the body in a locale of limited extent on the body. U.S. Pat. No. 1,191,664 is over fifty years old and describes a vibrating couch that does not attain sufficient gravitational force to stress the cells sufficiently to enhance their performance and it does not teach attaining 2G's for that purpose. U.S. Pat. No. 1,784,082 describes a massaging machine with means for imparting a vibratory motion to the superstructure on the machine and having an air cushion to allow a body to receive lighter vibrations. This patent notes that the vibrations cause relaxation of the muscles and stimulation of the circulation of the blood through the system, so it is apparent that this machine does not introduce higher gravitational forces on the cells of the body. U.S. Pat. No. 2,204,624 describes a massage table having massage rollers journalled in yokes and yieldably suspended for contact of the massage rollers with the body. The rollers move in groups reversely to each other so that a patient occupying the table is subjected to massaging action to stimulate circulation and relieve muscular disturbances, aches and pains.

U.S. Pat. No. 2,211,542 describes a motorized bed for vascular exercise, including a means for rocking the bed. The bed has springs, however, which would prevent attaining sufficient gravitational force to stress the cells in accordance with this invention. U.S. Pat. No. 2,500,508 describes a physical therapeutic table having the capability of producing massage by vibrations of minor amplitude that do not increase the gravitational forces in any significant way to stress the cells. The table employs a dynamically unbalanced shaft secured to the underside of the table near the center to impart mechanical vibrations. U.S. Pat. No. 2,506,183 describes an apparatus for colonic therapy; in particular cooperating appurtenances for intestinal treatment such as introduction of a liquid for cleansing irrigation, medication or other purposes. This patent describes positioning the patient's body to effect gravitation or physiological forces for irrigating the patient comfortably and notes that a more comfortably supported patient is in a more relaxed position to allow better penetration of the injected liquids with less pressure. U.S. Pat. No. 2,668,530 describes a vibration bed employing a vibrator to send vibrations through the springs and into a person resting on the bed. No increased gravitational forces are effected by this economical vibration bed. U.S. Pat. No. 2,696,207 describes a rocking hospital bed for treatment of diseases such as poliomyelitis, heart and respiratory disorders and other diseases. The descriptive matter in this patent makes clear that the therapeutic appliance rocks the hospital bed so that a variety of angles are attained with respect to a base which is mounted on wheels. There is no teaching in U.S. Pat. No. 2,696,207 of attaining 2 G's to sufficiently stress the cells to attain enhanced performance. U.S. Pat. No. 2,821,191 describes a pulsating device that has a music-playing means underneath a tabular portion, such as a doctor's table having extensible frames. The music allegedly vibrates and soothes the body of the patient. U.S. Pat. No. 2,895,468 describes a sleep inducing device in which lateral vibrations are imparted to the mattress holder and a person sleeping thereon.

U.S. Pat. No. 3,022,520 shows a cradle reciprocating apparatus with springs or the like with a lulling motion for lulling a restless infant into sleep. This patent describes the lulling motion in sharp distinction with the invention in this application, where at least 2G's are effected for stressing cells to attain enhanced cell performance.

In addition to taking advantage of the enhanced performance of the cells subjected to acceleration or gravitational forces in excess of the standard gravitational force, this invention takes the beneficial effects of stress one step further in enhancing learning. Specifically, this invention exposes a person to one or both of visual (visible) and audial (audible) learning stimulus simultaneously with the cell excitation during an acceleration/deceleration cycle. The reinforcement of the learning stimulus, or enhancement of learning, is accomplished through the use of at least one of the interpretable information messages so as to be discernible by the person whose cells are being subjected to the excitation; or by the combined subjecting of the person to the discernible message and cell excitation greater than normal.

No known prior art has been found showing the application of this invention.

Thus, as can be seen from the prior art, none of the prior art provides the benefits as provided in this invention. Specifically, the prior art fails to provide the structure for simultaneously effecting the stressing of up to the 2G's on a person in an adjustable position between sitting and reclining so as to obviate adversely effecting obese persons, persons with physical debilities, or aging persons who cannot experience more severe forms of exercise; and subjecting the person to a message to be learned with enhanced learning as a result of the stressing.

SUMMARY OF THE INVENTION

Accordingly, it is an object of this invention to provide a learning device that enhances learning capability by simultaneously showing a message to be learned and stressing the cells of a person's body, that positions their body on the device and activates a reciprocally moving apparatus to stress the cells, including the brain cells sufficiently to enhance their performance, as by stressing by gravitation and accelerational forces in excess of 1G (force of gravity).

It is a specific object of this invention to provide a learning device that has the capability of simultaneously subjecting a person to a learning stimulus and stressing body cells while simultaneously supporting the person's body in a predetermined position other than vertical to take advantage of the enhanced cell capability during the stressing of gravitational forces in excess of 1 G.

These and other objects will become apparent from the descriptive matter hereinafter, particularly when taken in conjunction with the appended drawings.

In accordance with this invention, enhanced learning is effected by apparatus and method that takes advantage of the enhanced cell performance, particularly brain cells when subjected to gravitational or accelerational forces greater than 1G for enhanced learning. The enhanced learning apparatus may employ audio- or visual- stimulus, or both, in synchronization with the reciprocal stressing of the cells.

BRIEF DESCRIPTION OF THE DRAWINGS

FIG. 5 is a top plan view of the couch assembly in accordance with one embodiment of this invention.

FIG. 6 is a side elevational view of the supporting sections of the couch assembly embodiment of FIG. 5.

FIG. 7a is a front view of the cam employed in accordance with embodiments of this invention.

FIG. 7b is a side elevational view of the cam of FIG. 7a.

FIG. 8a is a front view of the rigging-cam and roller assembly in accordance with one embodiment of this invention.

FIG. 8b is a side elevational view of the rigging-cam and roller assembly of FIG. 8a.

DESCRIPTION OF PREFERRED EMBODIMENT

Figure 1:
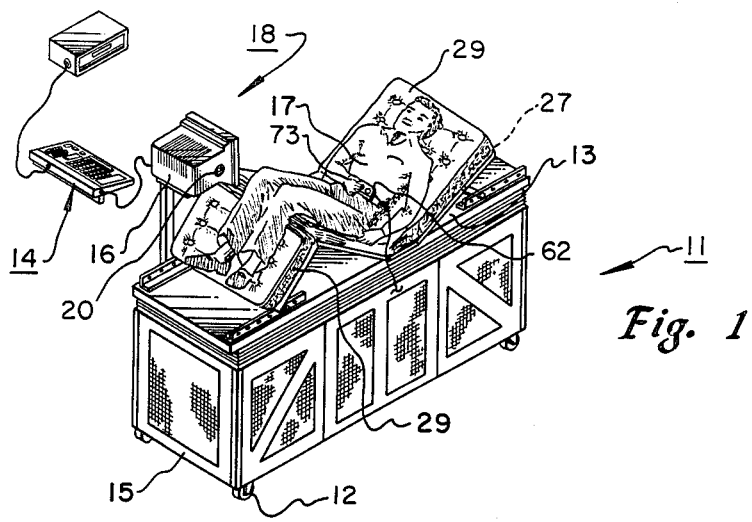
FIG. 1 is an isometric view of an embodiment of this invention in which the person whose body will be subjected to accelerational/gravitational type stress also has the brain cells stimulated by an audio-visual educational stimulus, the means displaying, or playing, the audio and the visual stimulii being affixed to the apparatus adapted to impart accelerational/gravitational forces in excess of 1G.

Before discussing a specific structure for carrying out this invention, it is believed helpful to look at some of the theories explaining the benefits of this invention. There are a plurality of governmental reports from a variety of governmental agencies delineating the improved consequences of stressing cells through gravitational variations, or their respective equivalent accelerational variations.

From the reports it seems clear that one beneficial objective would be to increase the strength and circulation benefits recognized by the stressing at forces above 1G without experiencing damage to the skeletal structure such as done by jogging, rebounding or jumping on a trampoline. A brief look at a variety of texts and reports confirms the benefits. The following quotations are taken from the book "THE MIRACLES OF REBOUND EXERCISE," noted hereinbefore. That book notes that if you increase the G-forces by twenty-five percent (25%), it is important to realize that every cell in the body is directly effected by that twenty-five percent increase in G-force and that the cells enhance their performance to an increased level if a controlled stress below the rupture threshold of the cells is introduced a number of times. The repetiton of stressing the cells causes the cells to begin to adjust and become more effective in their job; for example, strength or muscle cells become stronger. That book notes that although jogging has been believed to be an excellent exercise for cardiovascular system, it is, according to experts, devastating to the skeletal structure. That book goes on to extol the virtues of rebounding exercise and the beneficial effects that rebounding has on the cells. The book notes that muscles must not become fatigued if the benefical effects are to be achieved, but provides no means for achieving this end result. That book also reports that after two weeks of weightlessness in outer space, astronauts lost up to fifteen percent (15%) of the bone mass from their skeletal systems. The book goes on to report suprisingly improved results where even the cells associated with the eye become stronger and develop better vision in people practicing reboundology or jumping on the trampoline. The book contains the following quote which is believed most important. "Since each cell already knows its own function, any increased stimulation will cause the cell to memorize and function more efficiently in its specialization (emphasis added)." Regardless of whether or not the theories are correct, the benefits of this invention have been observed and do not depend upon any such theory for operational capability. Expressed otherwise, the theories given herein are merely by way of explanation and do not affect the scope of the invention being claimed.

This invention permits the person to enhance their learning through enhanced functioning of each body cell which will automatically adjust to work to its maximum capability under the stressing to which it is subjected. Expressed otherwise, the cells adapt to the different forces created on them by the accelerational/decelerational forces to which they are subjected. Consequently, if the body is subjected to gravitational forces of from 0 to 2G's the cells will essentially double their strength or effectiveness in contrast to a 1G effect that they normally feel. Moreover, the person will have improved learning, have sharper memory retention and otherwise demonstrate enhanced learning because of gravitational or accelerational stressing of the cells; for example, the brain cells. This invention is designed to stress the cells and effect the improved benefits of differential gravitational force, or accelerational force, larger than the normal 1 G force, yet allow invalids, people with lower back problems, obese people, arthritic people or the like to obtain the same benefits without worsening their physical debilities.

In my copending patent application Ser. No. 06/752,971, entitled "Induced Gravitational Force Accelerator/Decelerator Exerciser," I disclosed an apparatus for exercising the body by using the advantages of enhanced cell performance without the disadvantages of worsening physical debilities or the like. Several of the patents discussed hereinbefore were cited against that patent application. The descriptive matter of that copending patent application is incorporated herein by reference for any information that may be omitted herefrom. On the other hand, for readers convenience most of the information will be duplicated herein with regard to the reciprocal mechanism and the body support.

Referring to the FIGS., and particularly FIG. 1, there is illustrated an exerciser 11 comprising two main subassemblies including support means 13 on a top for supporting a body in a predetermined position and adapted to be moved reciprocally and vertically with a body thereon; and a reciprocating means 15 for moving the support means and the body reciprocally vertically such that increased and decreased accelerational/gravitational forces are effected on the support means and the body, thereby sufficiently stressing the cells to achieve the beneficial results of enhanced cell performance delineated hereinbefore. A body 17 reposes on the support means 13 so as to be moved therewith; such that there is realized the beneficial effects of the gravitational force acceleration/ deceleration stresses by the reciprocating means 15. The overall learning device 18, includes, in addition to the exerciser 11, a computer 14 having a visual display 16 and an audio speaker 20. In the illustrated embodiment, the learning device 18 has wheels 12 to make it in a form analogous to a hospital bed or the like that can be rolled around as needed.

The wheels 12 are designed to withstand the forces that be created by reciprocating movement of the person. Ordinarily, it may be advisable to employ brakes on the wheels similar to the conventional brakes employed on hospital beds so as to prevent forward and rearward motion of the learning device 18 during the stressing of the cells of the body 17 of the person thereon.

The support means 13, FIGS. 1, 2, 5 and 6 may comprise any structure suitable to support the body 17 in a predetermined position. As illustrated in the designated Figures, the support means 13 is movable between a substantially planar position so as to support a body in the horizontal, or prone position, a sitting position for supporting the body in a semi-prone or sitting position, or to any position in between. Specifically, the support means 13 includes a plurality of articulated sections 19, 21, 23, 25, FIGS. 5 and 6 that can be arranged in a position between a planar rigid sheet for supporting the body in the prone position into an illustrated couch for supporting a body in the semi-prone or sitting position. As illustrated in Figs. 1 and 6, the respective sections may be arranged to comprise a rigid sheet overlying reinforced support such as angle iron structure 27. The rigid sheet material may be metallic sheet such as sheet metal or a combination of metallic sheet with plywood and the like for greater rigidity. As illustrated in FIG. 1, the entire couch assembly may be positioned over a layer of planar material supported on a structural skeleton, such as of square tubular members, for effecting the necessary amplitude and frequency of reciprocation to introduce the desired G-forces onto the cells.

Onto the respective sections 19, 21, 23 and 25, there is imposed a mat 29, FIG. 1. The mat 29 includes about four to six inches of padding, such as foam padding, held in place and covered by a cover. The padding may take any form such as foam rubber, polystyrene foam, polyurethane foam or more dense and more nearly solid foam. It should have the effect of cushioning the body, particularly the bodies of obese or arthritic people. The cover may be of any type of covering including cloth, vinyl, leather or the like. Vinyl is easily cleaned, resistant to stains and economical, so it is a preferred form of cover. Preferably, the mat has a supporting form such as a pillow for supporting the knees or the like to prevent exacerbation or back problems or the like because of lack of support to any part of the anatomy during the mechanically induced accelerational/decelerational forces. Of course, belts similar to seat belts can be employed for a more secure feeling by the user if desired.

The reciprocating means 15 may comprise any suitable structure that is capable of inducing the desired frequency and magnitude of vertical reciprocal movements to be able to induce the gravitational force accelerator/decelerator stressing of the cells to the support means 13.

The reciprocating means 15 is supported by way of a structural framework. The structural framework may comprise a variety of different types of structures having adequate strength. For example, steel plate about one-fourth inch thick may be employed for the motor supports and the like. All of the plates can be drilled in a standard way desired to achieve uniformity and interchangeability. If desired, on the other hand, other metallic meterials such as aluminum can be employed for lighter weight.

Figure 2:
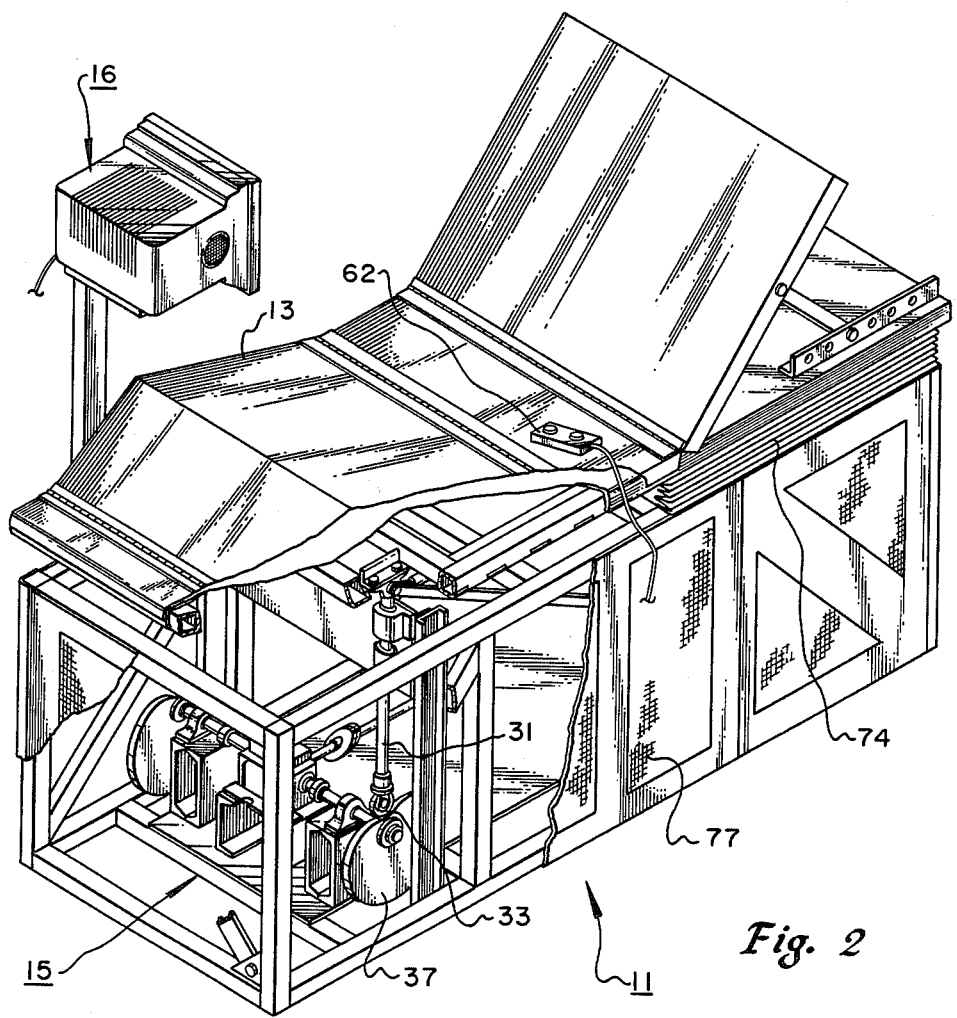
FIG. 2 is a partial isometric, partly cut away for simplicity, showing the embodiment of FIG. 1 without the person, padding and the computer control.
Figure 4:
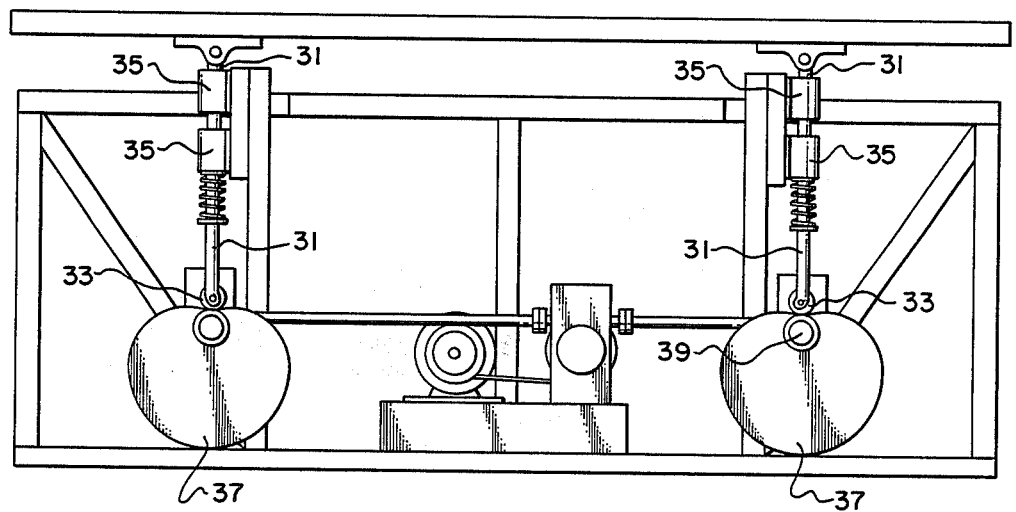
FIG. 4 is a side elevational view, partly cut away to show the essential apparatus, in accordance with one embodiment of this invention, for example, the embodiment of FIG. 2.

As illustrated, the reciprocating means 15 includes lifting rods 31, FIGS. 2 and 4. They are supported, in turn, on respective cam follower rollers 33. The lifting rods 31 are slidably mounted in supports 35, FIG. 4, so as to move vertically reciprocally responsive to the up and down movement of the cam follower rollers 33 riding on cams 37 at each of the respective corners.

Figure 3:
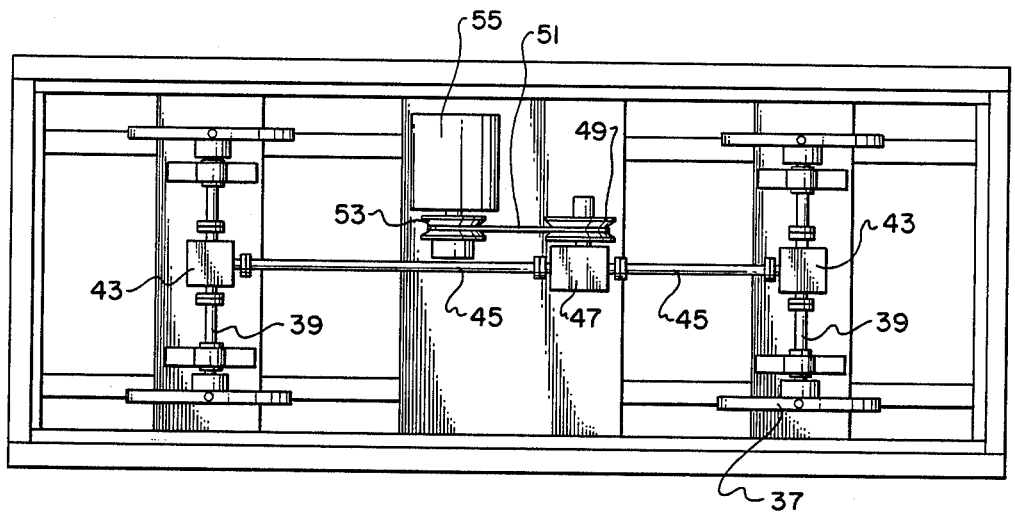
FIG. 3 is a top plan view, partly cut away, showing the embodiment of FIG. 2.

Each cam 37 is connected rigidly with the drive shaft 39 as by the cam roller assembly 41, FIGS. 8a and 8b, keys and slots or the like. Through similar arrangement, each of the cams rotate as their respective shafts 39 rotate responsive to power from a transmission 43, FIG. 3, at each end. Each of the transmissions 43 is caused to transmit torque; and, hence, rotate the shafts 39 by respective drive shafts 45 from the variable speed transmission 47. The variable speed transmission 47 has a variable diameter sheave 49 that has halves that can be closer together or farther apart to give variable diameter to the drive driven by belt 51 coming from the pulley 53, in turn driven by an electric motor 55. In this way the repetitions per minute (RPM's) can be varied even with a constant speed electric motor 55. Expressed otherwise, the speed of the respective cams is slaved so they rotate in unison and at a desired repetition rate to get the desired repetition rate for the body given the acceleration/deceleration stress for stressing its cells.

If desired, a variable speed motor 55 can be employed and its speed can be controlled through a rheostat or the like on a control switch 62, FIGS. 1 and 2.

The respective cams 37 will have the same effective throw arm, or lobe size, although each respective sets of lobe sizes may be changed out to produce variable dimensions of displacements, or travel, as will be seen from the Tables 1, 2, and 3 hereinafter. Table 1 gives a typical range of amplitudes, or the respective throw sizes, and the repetitions rates for the apparatus of this invention to achieve the respective G loadings delineated.

TABLE 1

| | | (90 cycles/min) | | | | |
|---|---|---|---|---|---|---|
| | Table travel | Travel & Acceleration | | Body "G" Loads | | |
| Cam | (inches) | G max | G min | G max | G min | G |
| 1 | 8.7 | 1 | −1 | 2 | 0 | 2 |
| 2 | 6.525 | .75 | −.755 | 1.75 | .25 | 1.5 |
| 3 | 4.35 | .5 | −.5 | 1.5 | .5 | 1 |
| 4 | 2.175 | .25 | −.25 | 1.25 | .75 | .5 |

Table 2 shows the effect of speed in terms of repetitions, or cycles, per minture on a given cam, such as an 8.7 inch cam throw in terms of table acceleration and body G loads.

TABLE 2

| | | (cam 1) | | |
|---|---|---|---|---|
| Speed (cycles minutes) | Travel (inches) | Table Acceleration G max | Body "G" G max | Loads G |
| 90 | 8.7 | 1 | 2 | 2 |
| 80 | 8.7 | .79 | 1.79 | 1.58 |
| 60 | 8.7 | .44 | 1.44 | .88 |
| 40 | 8.7 | .19 | 1.19 | .38 |
| 20 | 8.7 | .05 | 1.05 | .1 |

Table 3 shows the displacement, velocity and acceleration analysis for harmonic motion cam using a base radius of 2.75 inches with a maximum displacement of 8.7 inches and a speed of 90 repetitions per minute (revolutions per minute of the cam in the illustrated embodiment.)

TABLE 3

| Degrees | Displacement (inches) | Velocity (in./sec) | Acceleration (in./sec$^2$) | G's |
|---|---|---|---|---|
| 0 | 0.000 | 0.000 | 386.395 | 2.000 |
| 5 | 0.017 | 3.573 | 384.925 | 1.996 |
| 10 | 0.066 | 7.119 | 380.525 | 1.985 |
| 15 | 0.148 | 10.611 | 373.229 | 1.966 |
| 20 | 0.262 | 14.022 | 363.093 | 1.940 |
| 25 | 0.408 | 17.326 | 350.193 | 1.906 |
| 30 | 0.583 | 20.499 | 334.628 | 1.866 |
| 35 | 0.787 | 23.515 | 316.516 | 1.819 |
| 40 | 1.018 | 26.353 | 295.996 | 1.766 |
| 45 | 1.274 | 28.990 | 273.223 | 1.707 |
| 50 | 1.554 | 31.406 | 248.370 | 1.643 |
| 55 | 1.855 | 33.583 | 221.627 | 1.574 |
| 60 | 2.175 | 35.505 | 193.197 | 1.500 |
| 65 | 2.512 | 37.157 | 163.298 | 1.423 |
| 70 | 2.862 | 38.525 | 132.155 | 1.342 |
| 75 | 3.224 | 39.601 | 100.006 | 1.259 |
| 80 | 3.595 | 40.375 | 67.097 | 1.174 |
| 85 | 3.971 | 40.842 | 33.676 | 1.087 |
| 90 | 4.350 | 40.998 | −0.000 | 1.000 |
| 95 | 4.729 | 40.842 | −33.677 | 0.913 |
| 100 | 5.105 | 40.375 | −67.097 | 0.826 |
| 105 | 5.476 | 39.601 | −100.007 | 0.741 |
| 110 | 5.838 | 38.525 | −132.155 | 0.658 |
| 115 | 6.188 | 37.157 | −163.298 | 0.577 |
| 120 | 6.525 | 35.505 | −193.198 | 0.500 |
| 125 | 6.845 | 33.583 | −221.627 | 0.426 |
| 130 | 7.146 | 31.406 | −248.370 | 0.357 |
| 135 | 7.426 | 28.990 | −273.223 | 0.293 |
| 140 | 7.682 | 26.353 | −295.996 | 0.234 |
| 145 | 7.913 | 23.515 | −316.516 | 0.181 |
| 150 | 8.117 | 20.499 | −334.628 | 0.134 |
| 155 | 8.292 | 17.326 | −350.193 | 0.094 |
| 160 | 8.438 | 14.022 | −363.093 | 0.060 |
| 165 | 8.552 | 10.611 | −373.229 | 0.034 |
| 170 | 8.634 | 7.119 | −380.525 | 0.015 |

TABLE 3-continued

| Degrees | Displacement (inches) | Velocity (in./sec) | Acceleration (in./sec²) | G's |
|---|---|---|---|---|
| 175 | 8.683 | 3.573 | −384.925 | 0.004 |
| 180 | 8.700 | −0.000 | −386.395 | 0.000 |
| 185 | 8.683 | −3.573 | −384.925 | 0.004 |
| 190 | 8.634 | −7.119 | −380.525 | 0.015 |
| 195 | 8.552 | −10.611 | −373.229 | 0.034 |
| 200 | 8.438 | −14.022 | −363.093 | 0.060 |
| 205 | 8.292 | −17.326 | −350.193 | 0.094 |
| 210 | 8.117 | −20.499 | −334.628 | 0.134 |
| 215 | 7.913 | −23.515 | −316.516 | 0.181 |
| 220 | 7.682 | −26.353 | −295.996 | 0.234 |
| 225 | 7.426 | −28.990 | −273.222 | 0.293 |
| 230 | 7.146 | −31.406 | −248.370 | 0.357 |
| 235 | 6.845 | −33.583 | −221.627 | 0.426 |
| 240 | 6.525 | −35.505 | −193.197 | 0.500 |
| 245 | 6.188 | −37.157 | −163.298 | 0.577 |
| 250 | 5.838 | −38.525 | −132.155 | 0.658 |
| 255 | 5.476 | −39.601 | −100.006 | 0.741 |
| 260 | 5.105 | −40.375 | −67.097 | 0.826 |
| 265 | 4.729 | −40.842 | −33.676 | 0.913 |
| 270 | 4.350 | −40.998 | 0.000 | 1.000 |
| 275 | 3.971 | −40.842 | 33.677 | 1.087 |
| 280 | 3.595 | −40.375 | 67.097 | 1.174 |
| 285 | 3.224 | −39.601 | 100.007 | 1.259 |
| 290 | 2.862 | −38.525 | 132.155 | 1.342 |
| 295 | 2.512 | −37.157 | 163.298 | 1.423 |
| 300 | 2.175 | −35.505 | 193.198 | 1.500 |
| 305 | 1.855 | −33.583 | 221.628 | 1.574 |
| 310 | 1.554 | −31.406 | 248.370 | 1.643 |
| 315 | 1.274 | −28.990 | 273.223 | 1.707 |
| 320 | 1.018 | −26.353 | 295.996 | 1.766 |
| 325 | 0.787 | −23.515 | 316.516 | 1.819 |
| 330 | 0.583 | −20.499 | 334.628 | 1.866 |
| 335 | 0.408 | −17.326 | 350.193 | 1.906 |
| 340 | 0.262 | −14.022 | 363.093 | 1.940 |
| 345 | 0.148 | −10.611 | 373.229 | 1.966 |
| 350 | 0.066 | −7.119 | 380.525 | 1.985 |
| 355 | 0.017 | −3.573 | 384.925 | 1.996 |
| 360 | 0.000 | 0.000 | 386.395 | 2.000 |

If desired, grease fittings can be employed throughout the apparatus, although conventionally available permanently lubricated bearings, bushings and the like are readily available to facilitate assembly without requiring grease fittings on the respective shafts, joints and the like.

If desired, the structural outer cabinet can be covered by suitable cover, panels or the like that may be affixed by Rivnut fasteners, screws, bolts or the like to a supporting structural framework. Such Rivnut fasteners are commercially available from Fastner Sales Company, P.0. Box 9226, Fort Worth, Tex. 76107.

If desired, the bottom of the structure may have leveling means for adjusting its height with respect to stub type feet or wheels where employed with wheels. As will be apparent, the more expensive bed-type, rollabout means are not necessary if employed in the home or the like. For hospital use, however, it is preferable wheels be employed as illustrated in FIG. 1.

The synchronized periodic display either visually or audibly, or both will be obtained through either a microswitch which senses the movement of the support means and some connected element, through a feedback electric means or phaselock circuit sensing the pulsed electric field applied by the tachometer generator attached to the rotary drive wheel, or simply by synchronously cycling the reciprocating apparatus and a computer control to video display terminal. For example, a synchronously controlled video terminal such as described in the article in the WALL STREET JOURNAL of Dec. 5, 1984 touting the "subliminal suggestion and self-hypnosis for your computer" can be employed. As noted in both the articles and in the booklet on the use of the softward, which the inventor has purchased, it lets the user rig his computer to blink a message to be learned in any desired interval at any of many repetition rates, such as, thousands of times per day. Specifically, the repetition rate can be synchronized with the repetition rate of the movement of the learner such that the message is detected anytime the gravitational force on the cells of the learner is above 1G. This is a portion of a cycle, as set forth in Table 3, during which the cells of the body of the nearner is stressed above 1G could be synchronized with the video display terminal controlled by the cumputer to obtain enhanced learning. Such a learning message may comprise ordinary educational information or can be the self improvement type messages set forth in the book "GATHERING POWER . . . ," Dr. Keyes, Jr., et al.

If desired, any other type of synchronized visible or audible displays or both, can be employed, as desired. Other arrangements will occur to a user once the idea of the concomitant synchronized visual or audible stimulus and the accelerational/decelerational force stressing of the cells is given to men of average skill in this art. Such synchronized learning stimulus will be synchronized with the reciprocal motion such that the message to be learned will be given at least while the body is being passed through an accelerational/decelerational or gravity force in excess of 1G, as above 1.25G during the change in direction during the bottom of a cycle so the learning stimulus is applied to the brain cells, as by way of the eyes to obtain enhanced learning.

Conversely, if desired, the educational stimulus, or message to be learned can be denied the body at the top of the portion when the gravitational force is less than 1G. Ordinarily with the simple audible message, such denial of the stimulus at the top portion of the reciprocal movement is not necessary.

While the respective G forces and revolutions and displacements attaining the G forces are are shown they are no means exhaustive, since greater rotational speeds or greater accelerational forces, positive and negative can be obtained with different amplitudes, or distances, of vertical displacement.

A person using the apparatus, or learning device can stay on the apparatus as long as desired to obtain the desired results. Again, it is preferred that the apparatus of this invention be employed at least initially, under medical supervision of medical doctor, orthopedic doctors or the like.

The advantages of this invention is that obese persons, other persons with physical debilities, arthritic persons and the like can obtain the advantages of enhanced learning, or enhanced cell performance to strengthen their cells in the respective duties of the cells without suffering adverse physical effects. Such persons would thus learn more rapidly because of special benefits adduced by the learning device. Whereas a relatively rigid support means has been described hereinbefore, it is readily apparent that any suitable means can be employed attuned to the physique of the user as desired. If desired, for example, the body can be strapped in, with or without supplemental pillows, to obtain the benefits of subjecting it to the forces of decreased and increased gravitational forces.

Also, it is readily apparent that the cam followers can be enclosed in raceways if it is desired to pull the body downwardly, rather than depend upon the force of gravity to move the body downwardly.

It should be emphasized that this is not merely a vibrational apparatus. Rather it is a combination of a learning enhancement device with induced gravitational force accelerator/decelerator exerciser to employ the induced gravitational accelerational/decelerational forces to obtain enhanced learning, as well as other enhanced beneficial effects of stressing cells. In accordance with this invention, the accelerational/decelerational forces can be induced by any means. Such means may run the gamut from mechanical, through electro-mechanical, to hydraulically reciprocating movement of rams or the like as long as the desired amplitude and magnitude is effected to obtain the desired increased and decreased G forces to obtain enhanced learning.

The acceleration/deceleration forces must move like a sine wave if their velocity profile were plotted, such as produced by the rotational cam 37 to obtain beneficial advantages without deleterious disadvantages.

It should be noted that this invention is operable and effective whether or not employed in the area of physical improvement, or under the supervision of a doctor. If employed under the supervision of a doctor, it is designed not only in order to strengthen the body, enhance learning, but to tone and tighten the various muscles and organs of the body as noted hereinbefore in the cited book "THE MIRACLES OF REBOUND EXERCISE." Thus, this invention can be employed under suitable supervision to effect desired changes in shape, pressure, and the like of eyeballs or other similar cells; as well as to enhance learning capabilities. It is theorized that any other therapy that is normally employed by the medical profession which influences trauma physical effect or the like can be employed with this invention. Expressed otherwise, this invention enables invalids, obese people, people with back problems, arthritic people, people suffering from emphysema or the like a method of achieving the delineated advantages of rebound exercise in obtaining enhanced learning without suffering adverse physical effects.

In operation, the elements of the reciprocating means 15 and the support means 13 are assembled as illustrated in the Figures. Thereafter, the person seeking to effect enhanced learning will place themselves on the body support in a suitable position. The synchronous drive is effected so that the message to be learned is flashed on the display means 16 in visual form, or through the speaker 20 if audible learning is to be achieved. The desired speed drive control and the desired cam size are employed to get the amplitude, or reciprocal vertical distance. For example, if it is desired to have 0–2G's the person may have a cam of 8.7 inches and drive it at a speed of about 90 repetitions per minute. Suitable safety means such as belts or the like may be employed to constrain the body of the learner to the desired relaxed position.

From the foregoing, it can be seen that this invention achieves the objects delineated hereinbefore.

Although this invention has been described with a certain degree of particularity, it is understood that the present disclosure is made only by way of example and that numerous changes in the details of construction and the combination and arrangement of parts may be resorted to without departing from the spirit and the scope of the invention, reference being had for the latter purpose to the appended claims.

What is claimed is:

1. A learning device for accelerated learning by a person comprising:
   a. an induced gravitational force accelerator/decelerator mechanism for stressing the cells of the person's body, comprising:
      i. support means for supporting the body in a predetermined position under increased gravitational force and adapted to be moved reciprocally in a vertical direction for providing increased and decreased accelerational and gravitational force on the cells;
      ii. reciprocal means for moving said support means and body reciprocally such that increased and decreased accelerational and gravitational forces are exerted on said support means and cells of the body sufficiently to stress the cells above 1G, the force due to the earth's gravitational field, during a portion of the movement;
   b. an audio means for presenting an educational message in audio form audibly discernable by the person;
   c. a visual display means for presenting an educational message in visual form visually discernable by the person; and
   d. means for energizing said visual display means at least when the gravitational force from the body cells, including the brain cells is greater than 1G.

2. The learning device of claim 1 wherein said support means includes an adjustable seat means for sustaining the persons body in a desired position between sitting and reclining.

3. A learning device for accelerated learning by a person comprising:
   a. an induced gravitational force accelerator/decelerator for stressing the cells of a person's body, including the brain cells, consisting essentially of:
      i. support means for supporting the body in a predetermined position under increased gravitational force and adapted to be moved reciprocally in a vertical direction for providing increased and decreased gravitational force on the cells, including the brain cells,
      ii. reciprocal means for moving said support means and body thereon reciprocally such that increased and decreased gravitational forces are exerted on said support means and body sufficiently to stress the cells by subjecting them to accelerational and gravitational forces greater than 1G during at least a portion of the movement;
   b. a visual display means for presenting an educational message in visual form visibly discernable by the person; and
   c. means for energizing said visual display means at least when the gravitational force on the body cells, including the brain cells, is greater than 1G.

4. The learning device of claim 3 wherein said support means includes an adjustable seat means for sustaining the person's body in a desired position between sitting and reclining.

5. The learning device of claim 3 wherein said visual display means includes a computer means and a visual display board connected therewith.

* * * * *